United States Patent
Koh et al.

(10) Patent No.: US 7,844,333 B1
(45) Date of Patent: Nov. 30, 2010

(54) PACING THERAPY FOR TRANSIENT ISCHEMIA TREATMENT

(75) Inventors: Steve Koh, South Pasadena, CA (US); Euljoon Park, Valencia, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 873 days.

(21) Appl. No.: 11/736,155

(22) Filed: Apr. 17, 2007

(51) Int. Cl.
*A61N 1/365* (2006.01)
(52) U.S. Cl. ............................................ 607/17; 607/3
(58) Field of Classification Search ................... 607/30, 607/31, 25, 17

See application file for complete search history.

(56) References Cited

U.S. PATENT DOCUMENTS

| 5,716,382 | A | 2/1998 | Snell |
| 5,974,341 | A | 10/1999 | Er et al. |
| 6,865,420 | B1 | 3/2005 | Kroll |
| 7,010,347 | B2 | 3/2006 | Schecter |
| 2005/0192637 | A1* | 9/2005 | Girouard et al. ............... 607/3 |
| 2007/0150015 | A1* | 6/2007 | Zhang et al. .................. 607/17 |

* cited by examiner

*Primary Examiner*—Carl H. Layno
*Assistant Examiner*—Jon-Eric C. Morales

(57) ABSTRACT

Embodiments include methods and devices for detecting ischemia in a patient and treating the ischemia with a pacing therapy that increases cardiac efficiency, output, or both, without substantially increasing myocardial oxygen consumption. Such therapy may also be used to mitigate the adverse effects of decreased blood flow to the ischemic tissue by increasing the blood flow an oxygenation thereto.

16 Claims, 5 Drawing Sheets

PACING THERAPY FOR TRANSIENT ISCHEMIA TREATMENT

RELATED APPLICATION

This application is related to co-pending U.S. Ser. No. 11/467,894, filed Aug. 28, 2006, entitled "Cardiac Preconditioning Devices and Methods."

FIELD OF THE INVENTION

Embodiments of the present invention generally relate to implantable medical devices such as implantable electrical stimulation devices including pacemakers, implantable cardioverter/defibrillators (ICDs) and the like. In particular, embodiments of the invention are directed to implantable stimulation devices that are configured to treat transient ischemia in a patient with pacing therapy so as to improve cardiac output, efficiency or both without a substantial increase in cardiac oxygen consumption.

BACKGROUND

Cardiac ischemia is a condition that results from insufficient oxygenation to heart muscle and may pose an inherent risk in addition to potentially being a precursor to a life threatening event, such as myocardial infarction (MI). Detecting ischemia may be carried out by a variety of methods, some of which are amendable to implantable monitoring devices. Ischemia, and particularly, unstable ischemia, in a patient may be treated in a clinical setting by a variety of modalities.

A patient with severe unstable ischemia may be a candidate for immediate intervention, such as coronary angioplasty or bypass surgery. However, less severe cases may be treated by pharmaceutical methods as well as others. Even with such treatment modalities available, most ischemic events occur initially outside the clinical environment or at a place or time when such clinical assessment and treatment is not immediately available.

For ICD patients experiencing transient ischemia, standard ventricular pacing therapy in order to increase cardiac output is contraindicated as the increased heart rate induced as a result of the pacing will typically increase the oxygen demand on the heart tissue, and particularly the ischemic heart tissue, which may further exacerbate any damage caused by the ischemia. In addition, generally speaking, a paced rhythm is not as mechanically efficient as a normal sinus rhythm, and, as such, the blood flow output may even be further reduced. Thus, typical single chamber ventricle pacing therapy for an ischemic patient may increase oxygen demand of the heart tissue undergoing ischemic trauma and decrease the pumping efficiency of the heart overall or both.

As such, what has been needed are methods and devices for treating a patient with transient ischemia immediately after onset of the ischemia that do not generate a substantial increase in oxygen consumption by the heart.

SUMMARY

Some embodiments of a method of treating a patient's heart include detecting transient ischemia in the patient's heart and applying pacing therapy to the patient's heart which is configured to increase coronary artery blood flow without a substantial increase in oxygen consumption by the heart. Pacing therapy for some of these embodiments may include CRT pacing which may optionally be used in conjunction with increasing the pacing rate, increasing an amplitude of cathodic pacing pulses or increasing a pulse width of cathodic pacing pulses. Pacing therapy for some of these embodiments may also include synchronizing the initiation of cathodic pacing pulses at or near the time of lowest right atrial pressure.

Some embodiments of a method of treating a patient's heart include monitoring cardiac function parameters of the patient, detecting ischemia in the patient's heart, determining whether the detected ischemia is transient ischemia, applying pacing therapy to the patient's heart which is configured to increase coronary artery blood flow without a substantial increase in oxygen consumption by the heart, monitoring the level of ischemia during the application of pacing therapy and ceasing the application of pacing therapy when resolution of the transient ischemia has occurred. Pacing therapy for some of these embodiments may include CRT pacing which may optionally be used in conjunction with increasing the pacing rate, increasing an amplitude of cathodic pacing pulses or increasing a pulse width of cathodic pacing pulses. Pacing therapy for some of these embodiments may also include synchronizing the initiation of cathodic pacing pulses at or near the time of lowest right atrial pressure.

Some embodiments of an implantable stimulation device for treating a patient's heart include a pulse generator, an ischemia detector and a microcontroller in communication with the pulse generator and the ischemia detector which is configured to generate a stimulation signal from the pulse generator to deliver pacing therapy to the patient's heart upon detection of transient ischemia which is configured to increase cardiac output without a substantial increase in cardiac oxygen consumption. Pacing therapy for some of these embodiments may include CRT pacing which may optionally be used in conjunction with increasing the pacing rate, increasing an amplitude of cathodic pacing pulses or increasing a pulse width of cathodic pacing pulses. Pacing therapy for some of these embodiments may also include synchronizing the initiation of cathodic pacing pulses at or near the time of lowest right atrial pressure. Some of these embodiments may also include an implantable stimulation system, having a right ventricular electrode in electrical communication with the pulse generator, a left ventricular electrode in electrical communication with the pulse generator and a sensing electrode in electrical communication with the ischemia detector.

These features of embodiments will become more apparent from the following detailed description when taken in conjunction with the accompanying exemplary drawings.

BRIEF DESCRIPTION OF THE DRAWINGS

FIG. 3 is a block diagram of portions of an embodiment of an external programmer for use in processing and displaying event codes, counters, IEGM signals and the like.

DETAILED DESCRIPTION

Embodiments discussed herein relate to cardiac pacing methods, cardiac sensing methods and associated devices designed to relieve a variety of conditions that result from cardiac disease as well as other conditions. In order to pace or otherwise impart electrically delivered therapy to a patient's tissue, such as heart tissue, an electrical lead or delivery system is typically required. An electrical lead is used to deliver a therapeutic signal from a stimulation device to a target tissue site of the patient's body. Following is a general discussion of stimulation device embodiments that may be used with electric lead and stimulation method embodiments discussed herein.

Overview of Stimulation Device Embodiments

Figure 1:
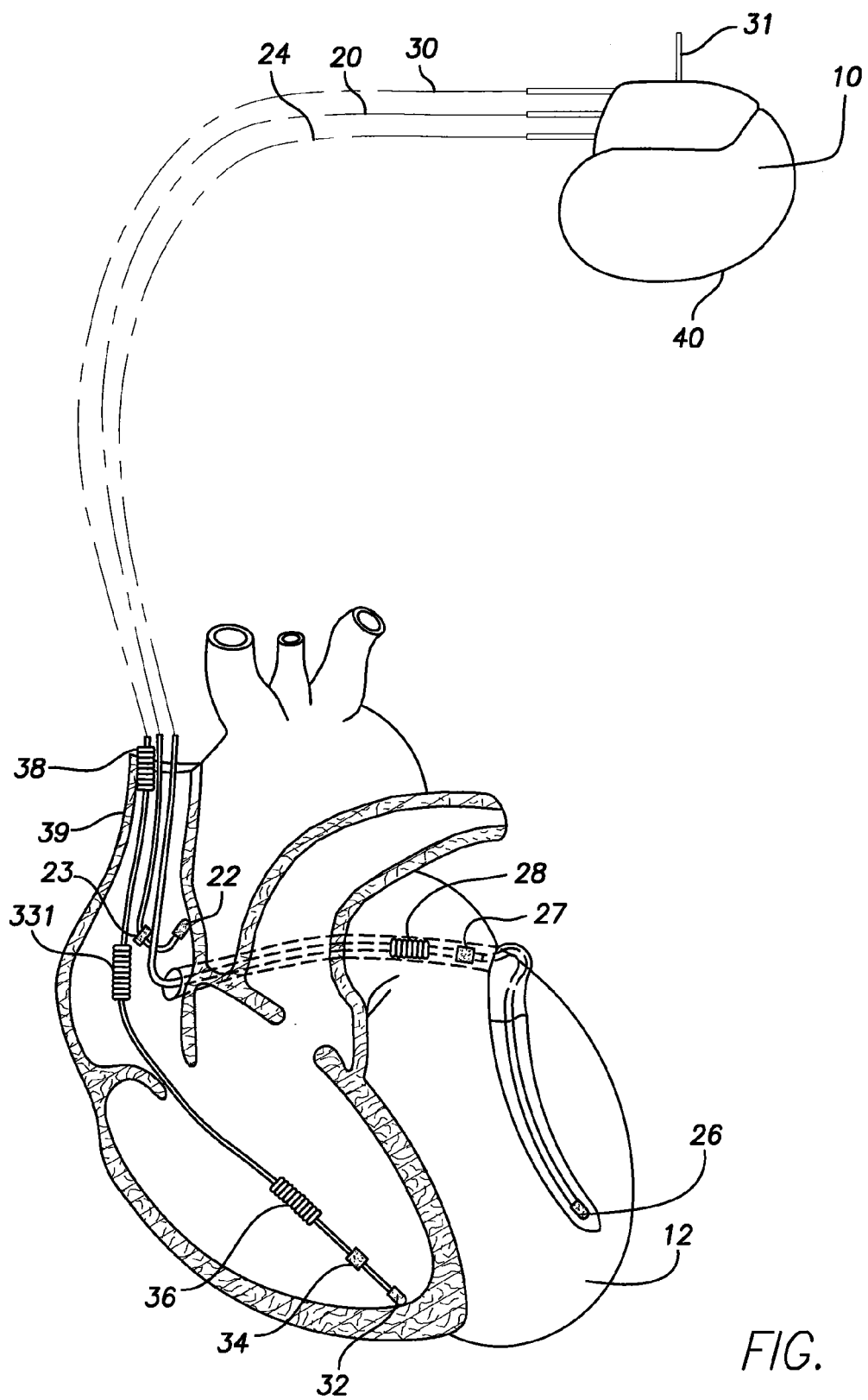
FIG. 1 is a simplified diagram illustrating an implantable cardiac stimulation device in electrical communication with at least three electrical leads implanted into the heart of a patient.

FIG. 1 shows a stimulation device 10 in electrical communication with the heart 12 of a patient with three electrical leads, 20, 24 and 30, in a configuration suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava 39. Accordingly, the right ventricular lead 30 is capable of receiving cardiac signals, and delivering stimulation in the form of pacing and shock therapy to the right ventricle. The stimulation device 10 includes an outer housing 40 that may be electrically conductive.

Figure 2:
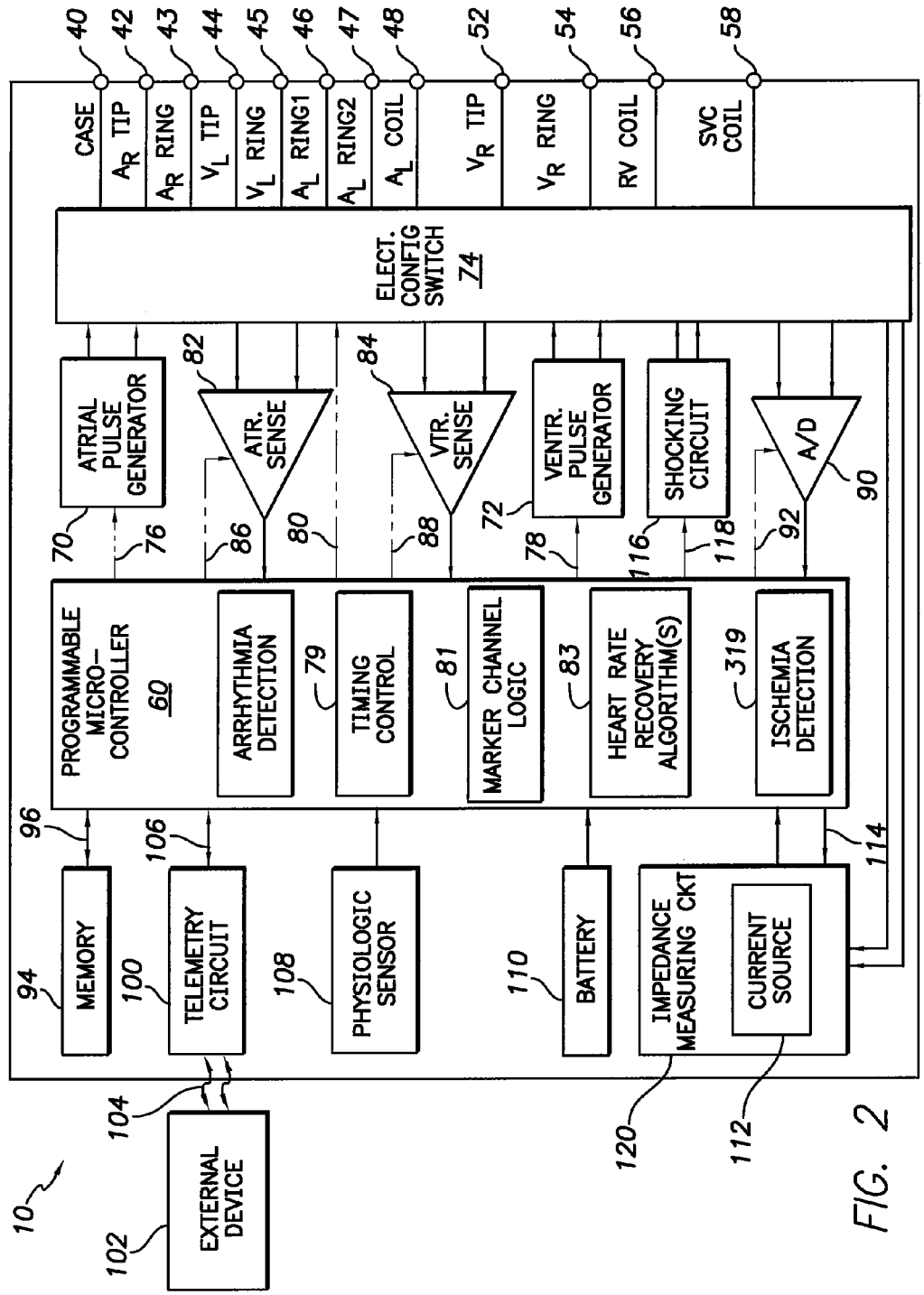
FIG. 2 is a functional block diagram of a multi-chamber implantable stimulation device illustrating exemplary basic elements of a stimulation device which can provide cardioversion, defibrillation, and/or pacing stimulation in up to four chambers of the heart.

As illustrated in FIG. 2, a simplified block diagram is shown of the multi-chamber implantable cardiac stimulation device 10, which is capable of treating both fast and slow arrhythmias with stimulation therapy, including cardioversion, defibrillation, and pacing stimulation. While a particular multi-chamber device is shown, this is for illustration purposes only, and appropriate circuitry may be duplicated, eliminated or disabled in any desired combination to provide a device capable of treating the appropriate chamber(s) with cardioversion, defibrillation and pacing stimulation. In addition, some processing step embodiments discussed below may be implemented in the form of software instructions that are resident on a computer-readable media that is included with the stimulation device 10.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 45, 46, 47, 48, 52, 54, 56 and 58 (shown schematically and, for convenience, the names of the electrodes to which they are connected are shown next to the terminals). While it is recognized that the number of terminals of current devices may be limited due to international standards, some terminals/electrodes may be programmably eliminated/selected in order to accommodate various embodiments. In addition, standards may change in the future and accommodate additional configurations.

To achieve right atrial sensing and pacing, the connector includes at least a right atrial tip terminal ($A_R$ TIP) 42 and a right atrial ring terminal ($A_R$ RING) 43, adapted for connection to the atrial tip electrode 22 and atrial ring electrode 23, respectively. To achieve left chamber sensing, pacing and shocking, the connector includes a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a controller in the form of a programmable microcontroller 60, which controls the various modes of stimulation therapy. The microcontroller 60 (also referred to herein as a controller or control unit) includes a microprocessor, or equivalent control circuitry, designed specifically for detecting sensed cardiac function data, generating warning signals that may be felt, heard or seen by a patient, controlling delivery of stimulation therapy as well as other function and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein. Microprocessor-based control circuits for performing timing and data analysis functions may be used.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. In order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 also includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, blanking intervals, noise detection windows, evoked response windows, alert intervals, marker channel timing (via marker channel logic 81), etc. Some embodiments of the microcontroller 60 are programmed with one or more heart rate recovery algorithms 83. The heart rate recovery algorithm(s) operate to monitor a patient's heart rate recovery when, for example, the patient recovers from a period of exercise to a period of rest. The algorithms can then save data associated with the heart rate recovery.

Switch bank 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, combipolar, etc.) and various shocking vectors by selectively closing the appropriate combination of switches (not shown). Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. The atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches. In this way, the clinician may program the sensing polarity independent of the stimulation polarity.

Each sensing circuit, 82 and 84, preferably employs one or more low power, precision amplifiers with programmable gain and/or automatic gain control, band pass filtering, and a threshold detection circuit to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the stimulation device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia or other clinical condition. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). The atrial and ventricular sensing circuits 82 and 84 receive control signals over signal lines 86 and 88 from the microcontroller 60, for controlling gain, threshold, polarization charge removal circuitry, and the timing of any blocking circuitry coupled to the inputs of the atrial and ventricular sensing circuits 82 and 84.

Cardiac signals may also be applied to the inputs of an analog-to-digital (A/D) data acquisition system 90. The data acquisition system 90 may be configured to acquire intracardiac electrogram signals, convert the raw analog data into a digital signal, and store the digital signals for later processing and/or telemetric transmission to an external device 102. The microcontroller 60 enables the data acquisition system 90 via control signal 92 to sample the cardiac signal that falls within a capture detection window. The data acquisition system 90 is coupled to the right atrial lead 20, the coronary sinus lead 24, and the right ventricular lead 30 through the switch 74 to sample cardiac signals across any pair of desired electrodes. The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

The operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 allows intra-cardiac electrograms and status information relating to the operation of the device 10 (as contained in the microcontroller 60 or memory 94) to be sent to the external device 102 through an established communication link 104.

In some embodiments, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). A physiological parameter of the heart, which may be measured to optimize such pacing and to indicate when such pacing may be inhibited or terminated is the stroke volume of the heart. Accordingly, the microcontroller 60 responds by adjusting the various pacing parameters (such as rate, AV Delay, V-V Delay, etc.) at which the atrial and ventricular pulse generators, 70 and 72, generate stimulation pulses. A common type of rate responsive sensor is an activity sensor, such as an accelerometer or a piezoelectric crystal, which is mounted within the housing 40 of the stimulation device 10. While shown as being included within the stimulation device 10, the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may use lithium/silver vanadium oxide batteries.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. The microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38, as shown in FIG. 1. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As further shown in FIG. 2, the device 10 is shown as having an impedance measuring circuit 120 including an impedance measuring current source 112 and a voltage measuring circuit 90 (shown in FIG. 2 as an A/D converter), which may be enabled by the microcontroller 60 via a control signal 114 for providing stroke volume measurements of the heart 12. The current source 112 can provide an alternating or pulsed excitation current. The voltage measuring circuitry 90 may also take the form of, for example, a differential amplifier. The uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring a respiration parameter (for example, tidal volume, respiration rate, minute ventilation or volume, abnormal or periodic breathing); measuring thoracic impedance for determining shock thresholds and shock timing (corresponding to the diastolic time); detecting when the device has been implanted; measuring a cardiac parameter (such as, stroke volume, wall thickness, left ventricular volume, etc.); and detecting the opening of the valves etc.

External Programmer

Figure 3:
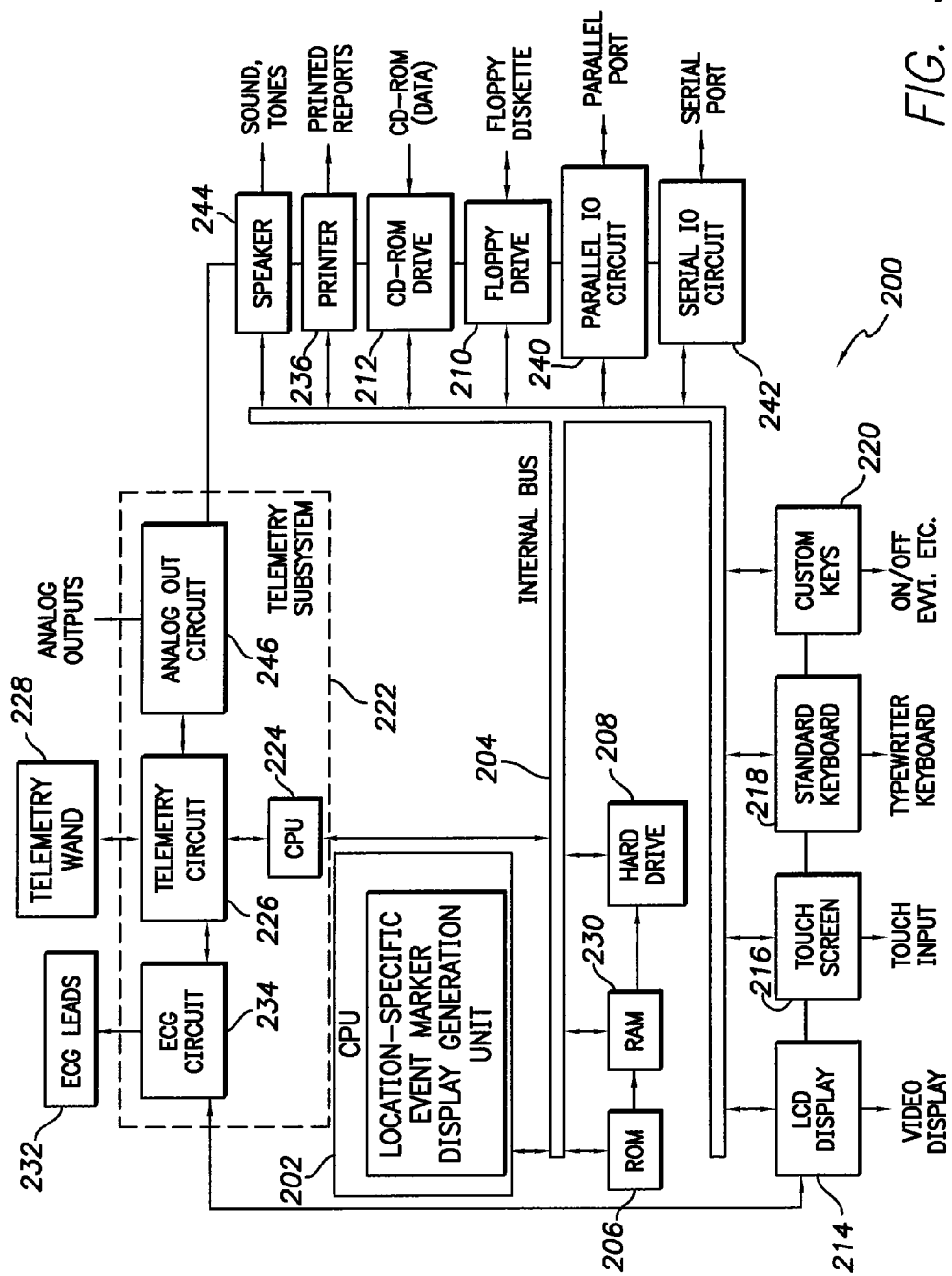

FIG. 3 illustrates pertinent components of an external programmer 200 for use in programming an implantable cardiac stimulation device such as the stimulation device 10 of FIGS. 2 and 3. Such programmer embodiments permit a physician or other user to program the operation of the implanted stimulation device 10 and to retrieve and display information received from the implanted device 10 such as IEGM data and device diagnostic data. In particular, the programmer 200 is provided with internal components capable of separately receiving, storing and processing event markers representative of events paced or sensed in any of the four chambers of the heart. Additionally, the external programmer 200 receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Operations of the programmer 200 are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an EWI key.

Typically, the physician initially controls the programmer 200 to retrieve data stored within the implanted cardiac stimulation device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via the internal bus. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device.

Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Preferably, all data stored within the implanted device is recorded within "event records" which facilitate the efficient storage and transmission of the data. The data provided by the stimulation device 10 and the event markers displayed by the external programmer 200 distinguish among a greater number of sensing locations, such as between the left and right chambers of the heart or among multiple locations within a single chamber of the heart.

For some embodiments, the memory of the external programmer 200 stores the location-specific event records, counter data and IEGM data for each of the four chambers of the heart received from the stimulation device 10. ROM 206 stores location-specific event records, counter data and IEGM data for each of the four chambers of the heart. A location-specific event marker display generation unit within the CPU controls the generation of graphic displays of diagnostic information based on the location-specific event records, counter data and IEGM data stored in ROM 206. The location-specific event processing unit maybe a software module of a control program executed by the CPU 202.

Data retrieved from the implanted stimulation device 10 is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device 10 may be further controlled to transmit additional data in real time as it is detected by the implanted device 10, such as additional IEGM data, lead impedance data, and the like. Additionally, or in the alternative, telemetry subsystem 222 receives ECG signals from ECG leads 232 via an ECG processing circuit 234. As with data retrieved from the implanted stimulation device 10 itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus the programmer 200 receives data both from the implanted device 10 and from the external ECG leads. Data retrieved from the implanted device 10 includes parameters representative of the current programming state of the implanted device. Under the control of the physician, the external programmer 200 displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Techniques for programming an implanted cardiac stimulation device may be found in U.S. Pat. No. 5,716,382 entitled "Programmer for an Implantable Cardiac Stimulating Device" filed Aug. 2, 1995, by S. Snell, which is incorporated by reference herein in its entirety. Prior to reprogramming specific parameters, the physician may control the external programmer to display any or all of the data retrieved from the implanted device or from the ECG leads, including displays of ECGs, IEGMs, and statistical patient information. In particular, the external programmer can be controlled to generate graphic displays or printouts of location-specific; IEGMs and event markers.

Depending upon the programming of the external programmer and the commands entered, the programmer may display either a single combined IEGM representative of a combination of the IEGM signals from the four chambers of the heart or may display the individual IEGM signals separately. Further information pertaining to information that may be displayed using the programmer may be found in U.S. Pat. No. 5,974,341 entitled "Method and Apparatus for Detecting and Displaying Diagnostic Information in Conjunction with Intracardiac Electrograms and Surface Electrocardiograms" filed Dec. 22, 1997, by S. Er et al. which is incorporated by reference herein in its entirety. Any or all of the information displayed by programmer 200 may also be printed using a printer 236.

Programmer 200 also includes a modem to permit direct transmission of data to other programmers via the public switched telephone network (PSTN) or other interconnection line, such as a T1 line or fiber optic cable. Depending upon the implementation, the modem may be connected directly to internal bus 204 or may be connected to the internal bus 204 via either a serial port 242 or a parallel port 240. Other peripheral devices may be connected to the external programmer via serial port 242 or a parallel port 240 as well. Although one of each is shown, a plurality of input output (IO) ports may be provided. A speaker 244 is included for providing audible tones to the user, such as a warning beep in the event the physician provides improper input. Telemetry subsystem 222 additionally includes an analog output circuit 246 for controlling the transmission of analog output signals.

Figure 4:
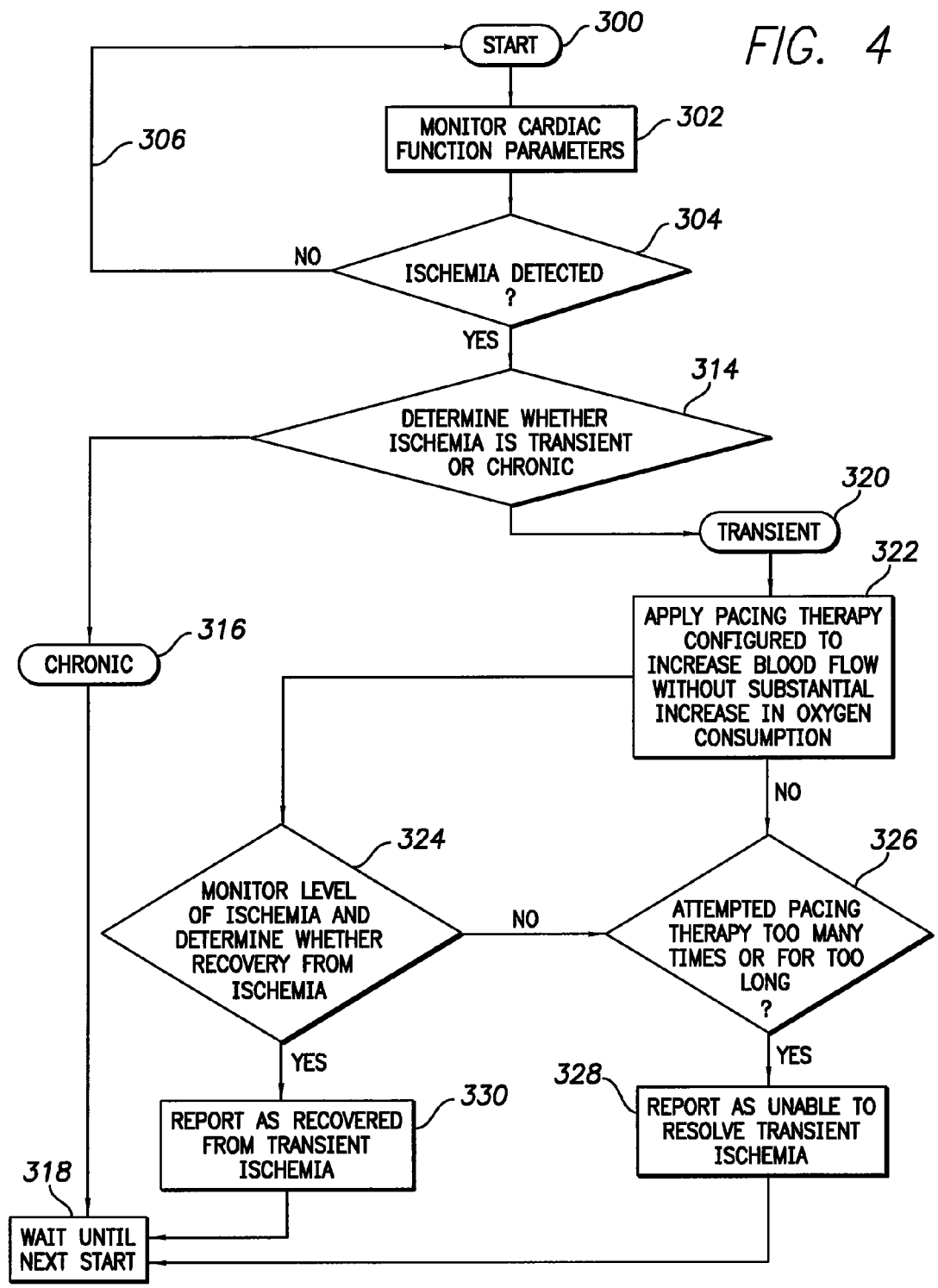
FIG. 4 shows a flowchart of a method of treating a patient.

With the programmer 200 configured as shown, a physician or other user operating the external programmer is capable of retrieving, processing and displaying a wide range of information received from the ECG leads or from the implanted device and to reprogram the implanted device 10 if needed. The descriptions provided herein with respect to FIG. 4 are intended merely to provide an overview of the operation of programmer 200 and are not intended to describe in detail each and every feature of the hardware and software of the device and is not intended to provide an exhaustive list of the functions performed by the device.

Ischemia Treatment

The microcontroller 60 of the stimulation device 10 discussed above may be configured for use with embodiments of methods for applying pacing therapy to a patient's heart in such a way as to increase an output, pumping efficiency, or both, of the patient's heart with no increase or no substantial increase in the oxygen consumption and workload of the patient's heart. Such pacing methods may be particularly useful after detection of transient ischemia in order to provide increased blood flow to the ischemic tissue which may prevent or reduce permanent damage to the ischemic tissue, and accelerate the healing of any damage to the insulted tissue.

Some patients, including patients having stimulation devices in the form of ICD devices implanted, have compromised heart function that may require pacing or defibrillation intervention by an implanted stimulation device, such as stimulation device 10. Typically, no pacing of the patient's heart is indicated for such patients so long as the natural sinus rhythm is providing adequate blood flow at an acceptable pulse rate. This is because the heart's natural sinus rhythm is generally more efficient at pumping blood than a rhythm produced by pacing, such as ventricular pacing, which initiates at the bottom of the ventricle instead of the atrium. However, if the patient's heart rate falls below about 40 ppm, right ventricular pacing may be initiated and continued until a natural sinus rhythm can be reestablished.

For ICD patients experiencing transient ischemia, standard ventricular pacing therapy is contraindicated as the increased heart rate induced as a result of the pacing will typically increase the oxygen demand on the heart tissue, and particularly the ischemic heart tissue, which may further exacerbate any damage caused by the ischemia. In addition, as discussed above, the paced rhythm is generally not as efficient as a normal sinus rhythm, and, as such, the blood flow output from the patient's heart into the aorta may even be further reduced unless the pacing rate is further increased further increasing the oxygen demand from heart tissue. Thus, typical single ventricle pacing therapy (RV or LV) for an ischemic patient may increase oxygen demand of the heart tissue undergoing ischemic trauma, decrease the pumping efficiency of the heart overall, or both.

Some studies have shown, however, that pacing therapy embodiments such as cardiac resynchronization therapy (CRT) may be useful to increase blood flow from the heart of a patient without a substantial increase in oxygen consumption by the heart tissue. CRT may typically be indicated in non-ischemic patients having an ejection fraction below about 35%, QRS duration greater than about 135 ms, high degree of left bundle branch blockage and high level of ventricular de-synchronization. In the absence of such factors, battery drain on the stimulation device 10 as well as other physiological factors and costs may weigh against the implementation of CRT pacing therapy generally in ICD patients.

The effects of CRT induced by either ventricular or biventricular pacing have been shown to result in both acute and chronic effects on a patient's body. Among the acute effects are enhancement of systolic function including an increase in systolic pressure, an increase in stoke volume, a reduction in LV end-systolic volume and an increase in LV pressure. In addition, an improvement in cardiac efficiency with a similar or lower level of oxygen consumption by the heart relative to a non-CRT treated heart has been observed. These acute effects have also been shown to quickly subside upon removal of the CRT stimulation.

In view of this, it may be useful to use CRT pacing in patients experiencing transient ischemia in order to increase blood flow to the ischemic tissue, thereby increasing oxygenation to the insulted tissue and accelerating the healing process, without substantially increasing the oxygen demand of the ischemic tissue or other cardiac tissue. As such, some embodiments of stimulation devices 10 may be configured to monitor cardiac function of the patient, and, upon detection of transient ischemia (as determined by ST segment elevation or any other suitable method), initiate a pacing therapy configured to increase blood flow without causing a substantial increase in oxygen demand by the cardiac tissue. Such pacing therapy may include CRT embodiments as well as other pacing therapy embodiments. During the delivery of these embodiments of pacing therapy, the stimulation device 10 may also be configured to continue to monitor the level and type of ischemia being experienced by the patient, and cease the pacing therapy upon the cessation or lessening of the ischemia to an acceptable level. The stimulation device 10 may also be configured to store clinical data acquired during the ischemic event and subsequent delivery of therapy. Such clinical data may include the amount of time required for recovery from the ischemic event.

FIG. 4 shows a flowchart illustrating a method of treating a patient who may be subject to episodes of transient ischemia. At the initiation of treatment, as indicated by block 300, the programmable microcontroller 60 of the stimulation device 10 monitors cardiac function parameters, as indicated in block 302, in order to detect whether ischemia is occurring in the patient's heart 12, as indicated by block 304. The monitoring of cardiac function parameters in order to detect or characterize ischemia may be carried out in conjunction with the monitoring of the same or other cardiac function parameters to detect and treat other cardiac conditions such as arrhythmias, tachycardia, bradycardia and the like. So long as no ischemia is detected, the patient's cardiac function parameters will continue to be monitored as indicated by loop 306. One method to detect whether ischemia is occurring in a patient's heart 12 is to monitor the cardiac function parameters for ST segment deviation, including ST segment elevation, as well as other cardiac function parameters. Although a deviated ST segment can be a good indicator of ischemia, other indicators such as heart rate, heart wall motion or blood $pO_2$ may also be monitored as independent sensing means or parameters. These parameters may also be used in addition to or in conjunction with a deviated ST segment in order to improve the reliability of ischemia detection. If the implantable stimulation device 10 is configured to monitor a patient's cardiac functions for such ST segment shifts, ischemia may be detected and further characterized.

Figure 5:
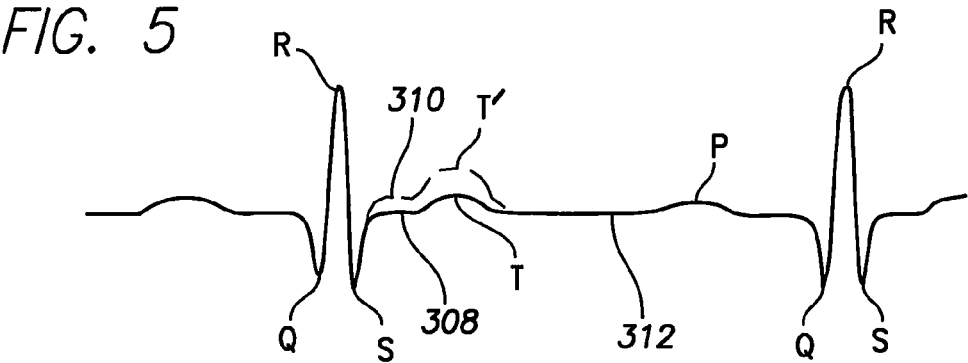
FIG. 5 illustrates a normal surface ECG pattern and also shows an elevated ST segment deviation which would be indicative of myocardial ischemia.
Figure 6:
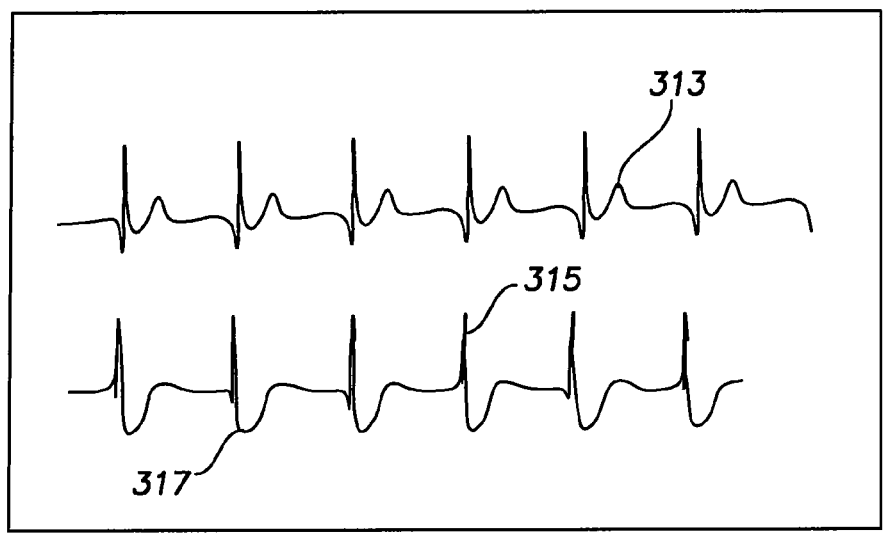
FIG. 6 illustrates a normal IEGM signal next to an IEGM signal which shows ST segment deviation which is indicative of myocardial ischemia.

With regard to ischemia detection via ST segment deviation, FIG. 5 illustrates a typical surface ECG electrogram signal from a pair of surface electrodes. The various portions of the electrogram are shown as the Q, R, S, T and P waves. These are all shown as portions of a solid line in FIG. 5. The normal ST segment 308 is also shown in FIG. 5. When coronary ischemia or a myocardial infarction occurs, there is a deviation of the ST segment 310 as shown by the dotted lines in FIG. 5. It is this deviation of the ST segment 310 as compared to the non-deviated segment 312 that is a clear indicator of coronary ischemia. Furthermore, it should be understood that the ST segment deviation could be either positive or negative depending upon the placement of the electrogram electrodes and where the ischemia occurred. FIG. 6 illustrates two IEGM signals taken from internally disposed electrodes within a patient's body. The non-ischemic IEGM signal 313 is shown above the IEGM signal 315 which has an ST segment deviation 317 which is indicative of myocardial ischemia. The IEGM signals shown in FIG. 6 may be collected with electrodes such as a right ventricular tip electrode 32 in conjunction with the housing 40 as a second electrode. The IEGM signal 317 may be indicative of a patient who has experienced significant myocardial ischemia for about 2 minutes to about 4 minutes. Such IEGM signals 315 may be evaluated by ischemia detection circuitry 319 of the programmable microcontroller 60, shown in FIG. 2. While a specific ischemia detection embodiment has been discussed above, the various elements of the devices and methods may be interchanged or reconfigured in any suitable manner in order to achieve the desired result. In addition, various other methods and devices may be used for ischemia detection. Commonly owned U.S. Pat. No. 6,865,420 filed Jan. 14, 2002, by M. Kroll, titled "Cardiac Stimulation Device for Optimizing Cardiac Output with Myocardial Ischemia Protection", which is incorporated by reference herein in its entirety, discusses embodiments of devices and methods for detection of ischemia which may be used in conjunction with some or all of the ischemia treatment embodiments discussed herein.

Referring again to FIG. 4, once ischemia is detected, the programmable microcontroller 60 then further processes cardiac function parameters and determines whether the ischemia is chronic or transient, as indicated in block 314. Such a determination may be based on a data log or other form of data gathered for a patient being treated for some embodiments. Chronic ischemia will generally be symptomatic and not be amenable to immediate treatment outside of a clinical environment under the supervision of a physician. Transient ischemia, may or may not be symptomatic, and may be amenable to immediate treatment. Methods for such characterization may include determining the magnitude of ST deviation, evaluating historical cardiac parameters specific to patient, and the like. If the ischemia detected is determined to be chronic, as indicated by block 316, it will generally be symptomatic and not be amenable to immediate treatment outside of a clinical environment under the supervision of a physician. As a result, the determination of the presence of chronic ischemia will end the treatment, as indicated by block 318. Even though ischemia treatment is terminated, it may be desirable for some embodiments of the stimulation device 10 to continue to monitor cardiac functions and parameters during the ischemic event and to store any clinical data obtained during the evaluation period for subsequent use by clinicians for treatment or intervention.

Once the ischemia detected is determined to be transient, as indicated by block 320, pacing therapy that is configured to increase blood flow, increase cardiac pumping efficiency, or both, with no substantial increase in oxygen consumption is initiated, as shown in block 322. For some embodiments, this type of pacing therapy includes CRT pacing that produces a synchronous contraction of the right and left ventricles of the patient's heart. During some CRT pacing embodiments, the stimulation device 10 transmits cathodic pacing pulses simultaneously to both the right and left ventricle of the patient's heart 12 so as to generate a substantially matching degree of systole over time in each ventricle. CRT pacing embodiments may be configured to allow for a beneficial difference in the timing of right and left ventricular contractions. For example, some embodiments of CRT pacing therapy applied after detection of transient ischemia may pace each ventricle of the patient's heart so as to optimize the relative delay between ventricles in order to achieve maximum cardiac pumping efficiency. The optimal amount of delay between ventricle pacing may vary from patient to patient. Cardiac pumping efficiency may be measured by parameters such as a velocity time integral (VTI) which is the product of blood velocity in the patient's aorta over time. A variety of pacing therapy embodiments, including CRT pacing therapy embodiments, may be used with the ischemia treatment methods and devices discussed herein. For example, commonly owned U.S. patent application Ser. No. 10/703,070, filed Nov. 5, 2003, by Min et al. and titled "Methods for Ventricular Pacing", which is incorporated by reference herein in its entirety, discusses a variety of pacing therapy methods and devices which may be used with the ischemia treatment devices and methods discussed herein. In general, the pacing pulses of pacing therapy delivered to the patient's heart may include biphasic or triphasic pulses which may also be configured to maintain a level of polarization which is acceptable for continuing to monitor cardiac function parameters during the application of pacing therapy. Cardiac function parameters may be monitored on an ongoing basis during the application of pacing therapy in order to continue to measure the level of ischemia present in the patient's heart 12 as therapy is being delivered or between delivery of pacing therapy doses.

Other pacing therapy method embodiments that may be used in conjunction with CRT pacing therapy for increasing blood flow, cardiac pumping efficiency, or both, include increasing the pacing rate, increasing the pulse width of cathodic pacing pulses and increasing the pulse amplitude of cathodic pacing pulses. Each of these parameters may be increased a predetermined percentage above a capture threshold level of these parameters. The predetermined percentages may be based on a variety of factors, including historical patient data and the like.

It may also be useful, in some treatment embodiments, to trigger the initiation of cathodic pacing pulses of the pacing therapy at or near the point of lowest right atrial (RA) pressure in order to maximize blood flow through the coronary vasculature. This pacing therapy, which may be used independently, or in conjunction with CRT pacing, may be sufficient to increase blood flow through the coronary vasculature without increasing the oxygen demand on the heart tissue. Such triggering, as opposed to the typical escape timing interval triggering, may be useful to improve overall blood flow through the coronary arteries without increasing the workload on the heart. The pressure in the right atrium is indicative of the end pressure of the coronary vasculature By triggering cathodic pacing pulses at or near the time of the lowest right atrial pressure, the peak to peak pressure differential is lowered but the average flow may be increased.

Figure 7:
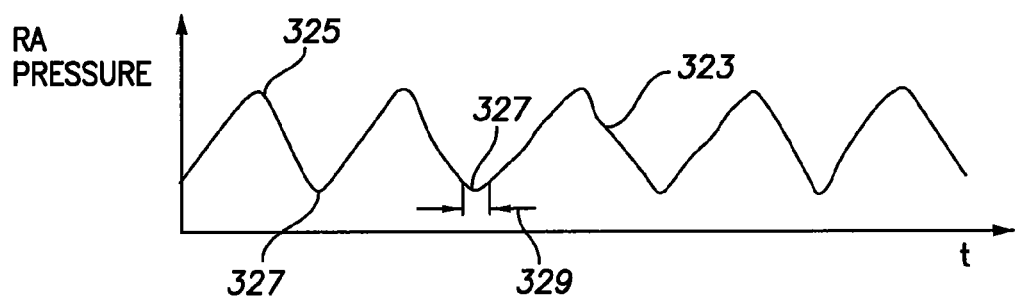
FIG. 7 shows a simplified measurement of right atrial pressure of a patient with respect to time.

FIG. 7 shows a simplified right atrial pressure signal 323 of a patient with respect to time. Right atrial pressure peaks 325 are indicative of maximum right atrial pressure for a given right atrial pressure signal 323. Pressure valleys 327 are indicative of minimum right atrial pressure for a given pressure signal 323. As discussed above, it may be useful to initiate cathodic pacing pulses of pacing therapy at the right atrial pressure minimums 327, or within a predetermined time or pressure range of the minimum 327, as indicated by arrow 329 in FIG. 7. For example, it may be useful to initiate cathodic pacing pulses of pacing therapy, including CRT pacing therapy, at the right atrial pressure minimum 327 or within a time period corresponding to predetermined pressure range near the minimum 327, as shown by arrow 329. It may also be useful for some embodiments of stimulation devices 10 to be configured to adjust the timing of pacing pulse initiation so as to optimize the timing based on previously collected pressure data, cardiac output function data or both with respect to a specific patient. Pressure measurements for such methods may be obtained with a pressure sensor, such as pressure sensor 331 disposed within the right atrium as shown in FIG. 1. Such a pressure sensor may be in communication with the microprocessor 60 of the implantable stimulation device 10 and include piezoelectric sensors, diaphragm sensors and the like.

While pacing therapy is being applied after detection of transient ischemia, cardiac function parameters may continue to be monitored to determine whether the patient has recovered from ischemia, as indicated in block 324. If transient ischemia continues, microprocessor 60 analyzes whether pacing therapy has been attempted more than a predetermined maximum number of attempts, or maximum predetermined amount of time, as indicated by block 326. If the transient ischemia continues to be detected, pacing therapy, as indicated in block 322 also continues. If the pacing therapy is determined to have gone on for a maximum predetermined time limit, this information may be reported or stored, as indicated by block 328, and pacing therapy stopped per block 318. If the monitoring of ischemia level per block 324 indicates that the patient has recovered from the transient ischemia or the transient ischemia has been otherwise resolved, this information may be reported or stored, as indicated by block 330, and pacing therapy ceased, as indicated by block 318. In either case, once therapy has stopped, the patient's cardiac function parameters may continue to be monitored to determine whether another episode of transient ischemia has begun.

Blocks 328 and 330 indicate a process collecting and reporting data during an ischemic episode and subsequent treatment as discussed above. Other data may also be collected by elements of the stimulation device 10, which may include recovery time from initial onset of ischemic episode. Such data may be stored in the memory 94 of the stimulation device 10 and may also be transmitted to the external programmer 300 through telemetry circuit 100 in order to make the information gathered immediately available for use by the patient or clinicians.

In general, a wide variety of techniques may be implemented consistent with the principles the embodiments discussed herein and no attempt is made herein to describe all possible techniques. Although described primarily with reference to embodiments wherein the implanted stimulation device is a defibrillation/pacer, the principles discussed herein are applicable to other implantable medical devices as well. The various functional components of the exemplary embodiments may be implemented using any appropriate technology including, for example, microprocessors running software programs or application specific integrated circuits (ASICs) executing hard-wired logic operations. With regard to the above detailed description, like reference numerals used therein refer to like elements that may have the same or similar dimensions, materials and configurations. While particular forms of embodiments have been illustrated and described, various modifications can be made without departing from the spirit and scope of the embodiments of the invention. Accordingly, it is not intended that the invention be limited by the forgoing detailed description.

What is claimed is:

1. A method of treating a patient's heart, comprising detecting transient ischemia in the patient's heart; and initiating cardiac resynchronization pacing therapy (CRT) to the patient's heart in response to detection of transient ischemia wherein initiating the cardiac resynchronization pacing therapy further comprises increasing an amplitude of cathodic pacing pulses delivered during the cardiac resynchronization therapy.

2. The method of claim 1 wherein the pacing therapy further comprises an increase in the pacing rate.

3. The method of claim 1 wherein detecting transient ischemia comprises detecting ST segment deviation.

4. The method of claim 1 further comprising monitoring the level of ischemia during the application of pacing therapy and ceasing the application of pacing therapy when a desired level of clinical improvement is achieved or a predetermined maximum treatment time period has elapsed.

5. A method of treating a patient's heart, comprising detecting transient ischemia in the patient's heart; and initiating cardiac resynchronization pacing therapy (CRT) to the patient's heart in response to detection of transient ischemia wherein the pacing therapy further comprises increasing a pulse width of cathodic pacing pulses of the pacing therapy.

6. A method of treating a patient's heart, comprising detecting transient ischemia in the patient's heart; and initiating cardiac resynchronization pacing therapy (CRT) to the patient's heart in response to detection of transient ischemia wherein the pacing therapy comprises synchronizing the initiation of cathodic pacing pulses at or near the time of lowest right atrial pressure.

7. A method of treating a patient's heart, comprising monitoring cardiac function parameters of the patient; detecting ischemia in the patient's heart; determining whether the ischemia is transient ischemia; initiating cardiac resynchronization pacing therapy (CRT) to the patient's heart in response to transient ischemia, wherein initiating the cardiac resynchronization pacing therapy further comprises increasing an amplitude and pulsewidth of cathodic pacing pulses delivered during the pacing therapy;
monitoring the level of ischemia during the application of pacing therapy; and
ceasing the application of pacing therapy when resolution of the transient ischemia has occurred.

8. The method of claim 7 wherein the pacing therapy further comprises increasing the pacing rate of the patient's heart.

9. The method of claim 7 wherein the pacing therapy comprises synchronizing the initiation of cathodic pacing pulses at or near the time of lowest right atrial pressure.

10. An implantable stimulation device for treating a patient's heart, comprising:
a pulse generator;
an ischemia detector; and
a microcontroller in communication with the pulse generator and the ischemia detector which is configured to generate a stimulation signal from the pulse generator to initiate cardiac resynchronization pacing therapy (CRT) to the patient's heart upon detection of transient ischemia, wherein the microcontroller is further configured to increase an amplitude of cathodic pacing pulses delivered during the cardiac resynchronization pacing therapy after transient ischemia is detected.

11. The device of claim 10 wherein the microcontroller is further configured to generate a stimulation signal that increases the patient's heart rate after transient ischemia is detected.

12. The device of claim 10 further comprising An implantable stimulation device for treating a patient's heart, comprising:
a pulse generator;
an ischemia detector;
a microcontroller in communication with the pulse generator and the ischemia detector which is configured to generate a stimulation signal from the pulse generator to initiate cardiac resynchronization pacing therapy (CRT) to the patient's heart upon detection of transient ischemia; and
a pressure sensor configured to communicate with the microcontroller and sense right atrial pressure of the patient and wherein the microcontroller is configured to deliver pacing therapy wherein the initiation of cathodic pacing pulses is substantially synchronized to coincide at or near the time of lowest right atrial pressure.

13. The device of claim 10 wherein the microcontroller is further configured to measure a level of the patient's ischemia via IEGM monitoring.

14. The device of claim 10 wherein the microcontroller is further configured to measure the level of ischemia by detecting ST segment deviation.

15. The device of claim 10 wherein the microcontroller is further configured to detect and record a recovery time from onset of ischemia in the patient.

16. An implantable stimulation device for treating a patient's heart, comprising:
- a pulse generator;
- an ischemia detector; and
- a microcontroller in communication with the pulse generator and the ischemia detector which is configured to generate a stimulation signal from the pulse generator to initiate cardiac resynchronization pacing therapy (CRT) to the patient's heart upon detection of transient ischemia wherein the microcontroller is further configured to increase a pulse width of cathodic pacing pulses delivered during the cardiac resynchronization pacing therapy after transient ischemia is detected.

* * * * *